(12) United States Patent
Ota

(10) Patent No.: US 9,706,919 B2
(45) Date of Patent: Jul. 18, 2017

(54) OPHTHALMOLOGIC APPARATUS AND METHOD FOR CONTROLLING THE SAME

(71) Applicant: CANON KABUSHIKI KAISHA, Tokyo (JP)

(72) Inventor: Yuji Ota, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 368 days.

(21) Appl. No.: 14/088,173

(22) Filed: Nov. 22, 2013

(65) Prior Publication Data
US 2014/0146287 A1 May 29, 2014

(30) Foreign Application Priority Data
Nov. 26, 2012 (JP) ................................. 2012-257553

(51) Int. Cl.
| | |
|---|---|
| *A61B 3/12* | (2006.01) |
| *A61B 3/14* | (2006.01) |
| *A61B 3/15* | (2006.01) |
| *A61B 3/00* | (2006.01) |

(52) U.S. Cl.
CPC .............. *A61B 3/14* (2013.01); *A61B 3/0008* (2013.01); *A61B 3/0091* (2013.01); *A61B 3/12* (2013.01); *A61B 3/152* (2013.01)

(58) Field of Classification Search
CPC ....... A61B 3/0091; A61B 3/14; A61B 3/0008; A61B 3/12; A61B 3/152
USPC ................. 351/206, 211, 214, 221
See application file for complete search history.

(56) References Cited

U.S. PATENT DOCUMENTS

| | | | | |
|---|---|---|---|---|
| 4,715,703 A * | 12/1987 | Cornsweet | ............... | A61B 3/12 351/205 |
| 4,917,486 A * | 4/1990 | Raven | ................. | A61F 9/00821 351/221 |
| 2006/0077346 A1* | 4/2006 | Matsumoto | .............. | A61B 3/12 351/214 |
| 2007/0253688 A1* | 11/2007 | Koennecke | ............ | A61B 3/152 396/18 |
| 2008/0123050 A1* | 5/2008 | Tanaka | ...................... | A61B 3/14 351/206 |
| 2012/0050679 A1* | 3/2012 | Kishida | ..................... | A61B 3/12 351/206 |
| 2013/0010261 A1* | 1/2013 | Plaian | ....................... | A61B 3/12 351/206 |

(Continued)

FOREIGN PATENT DOCUMENTS

| | | |
|---|---|---|
| CN | 102379681 A | 3/2012 |
| JP | S56-151929 A | 11/1981 |
| JP | H01-195838 A | 8/1989 |

(Continued)

*Primary Examiner* — Jordan Schwartz
(74) *Attorney, Agent, or Firm* — CANON USA, INC. IP Division

(57) ABSTRACT

An ophthalmologic apparatus includes a photographing optical system configured to photograph a fundus of a subject's eye via a focusing lens, a projection unit configured to project, via a mask portion including an opening, a focusing index corresponding to the opening, and a driving unit configured to drive the focusing lens along an optical path based on a position of an image corresponding to the mask portion and a position of a focusing index image corresponding to the opening in a fundus image of the subject's eye.

28 Claims, 12 Drawing Sheets

(56) References Cited

U.S. PATENT DOCUMENTS

2014/0132930 A1* 5/2014 Ogura .................. A61B 3/14
351/211

FOREIGN PATENT DOCUMENTS

| JP | H03-193026 A | 8/1991 |
| JP | H04-009137 A | 1/1992 |
| JP | 2002-125933 A | 5/2002 |
| JP | 2009172154 A | 8/2009 |

* cited by examiner

OPHTHALMOLOGIC APPARATUS AND METHOD FOR CONTROLLING THE SAME

BACKGROUND OF THE INVENTION

Field of the Invention

The present invention relates to an ophthalmologic apparatus for observing or photographing a fundus of a subject's eye, and a method for controlling the same.

Description of the Related Art

Conventionally, there is known an ophthalmologic apparatus for observing or photographing a fundus, which captures focusing index images split and projected at the fundus of a subject's eye, and detects a positional relationship among the focusing index images to perform autofocusing.

One of the plurality of focusing index images may be vignetted at the subject's eye due to a small pupil or a cataract of the subject's eye. To deal with this issue, Japanese Patent Application Laid-Open No. 2009-172154 discusses a method for performing autofocusing by using a difference between a visible focusing index image and a preset focusing reference position fixed to an image sensor when only one of two split and projected focusing index images can be captured.

SUMMARY OF THE INVENTION

According to an aspect of the present invention, an ophthalmologic apparatus includes a photographing optical system configured to photograph a fundus of a subject's eye via a focusing lens, a projection unit configured to project, via a mask portion including an opening, a focusing index corresponding to the opening, and a driving unit configured to drive the focusing lens along an optical path based on a position of an image corresponding to the mask portion and a position of a focusing index image corresponding to the opening in a fundus image of the subject's eye.

According to another aspect of the present invention, there is provided a method for controlling an ophthalmologic apparatus that includes a photographing optical system configured to photograph a fundus of a subject's eye via a focusing lens and a projection unit configured to project, via a mask portion including an opening, a focusing index corresponding to the opening. The method includes driving the focusing lens along an optical path based on a position of an image corresponding to the mask portion and a position of a focusing index image corresponding to the opening in a fundus image of the subject's eye.

Further features of the present invention will become apparent from the following description of exemplary embodiments with reference to the attached drawings.

DESCRIPTION OF THE EMBODIMENTS

A projection position of a focusing index image to a fundus may shift from the center of an image sensor due to the influence of a state (astigmatism or refractive error) of a subject's eye. Consequently, even when a visible focusing index image is matched with a preset focusing reference position fixed to the image sensor as in the case of the conventional technology, the focusing image may deviate from appropriate focusing adjustment. Thus, an exemplary embodiment of the present invention is directed to improvement of focusing adjustment accuracy when one of a plurality of focusing index images cannot be obtained.

An ophthalmologic apparatus according to the present exemplary embodiment includes a projection unit configured to project, via a mask portion including an opening, a focusing index corresponding to the opening. The ophthalmologic apparatus according to the present exemplary embodiment further includes a driving unit configured to drive a focusing lens along an optical path based on a position of an image corresponding to the mask portion and a position of a focusing index image corresponding to the opening in a fundus image of the subject's eye. This enables easy focusing adjustment even when there is only one focusing index image in the fundus image.

When there is a plurality of focusing indices in the fundus image of the subject's eye, the driving unit desirably drives the focusing lens along the optical path so that a predetermined positional relationship can be set among the plurality of focusing indices in the fundus. When the fundus of the subject's eye and the projection unit are optically conjugate with each other, the predetermined positional relationship is set among the plurality of focusing indices in the fundus.

Figure 11A:
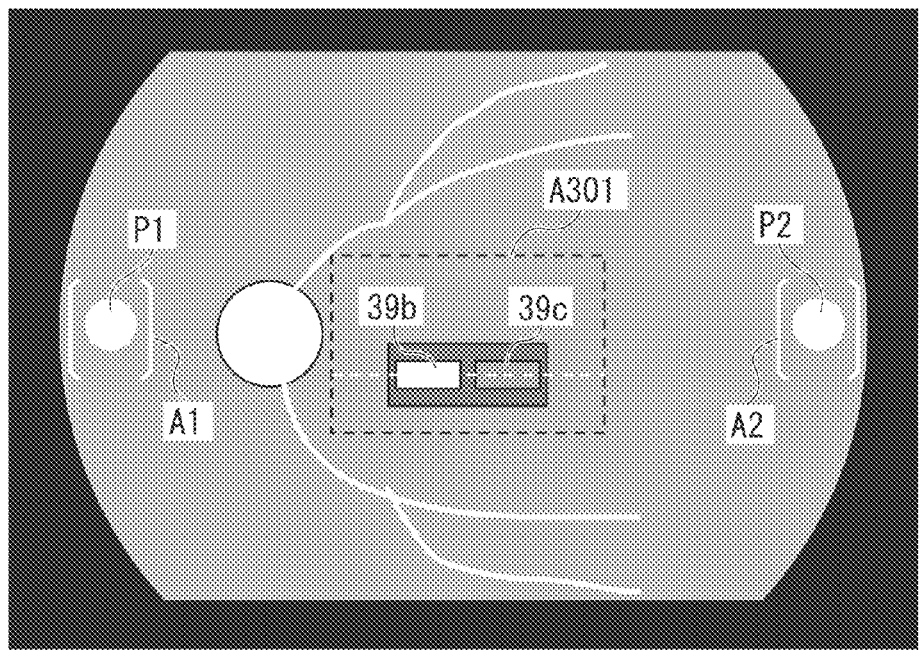
FIGS. 11A and 11B are diagrams each illustrating an example of a problem in a subject's eye, i.e., a refractive error, to be solved by the present exemplary embodiment.
Figure 11B:
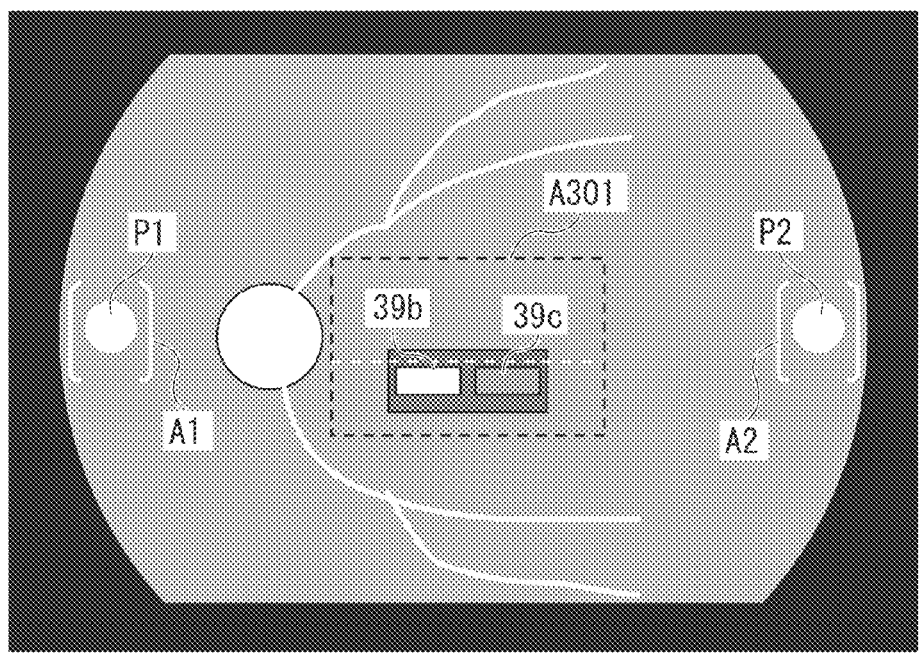
Figure 12A:
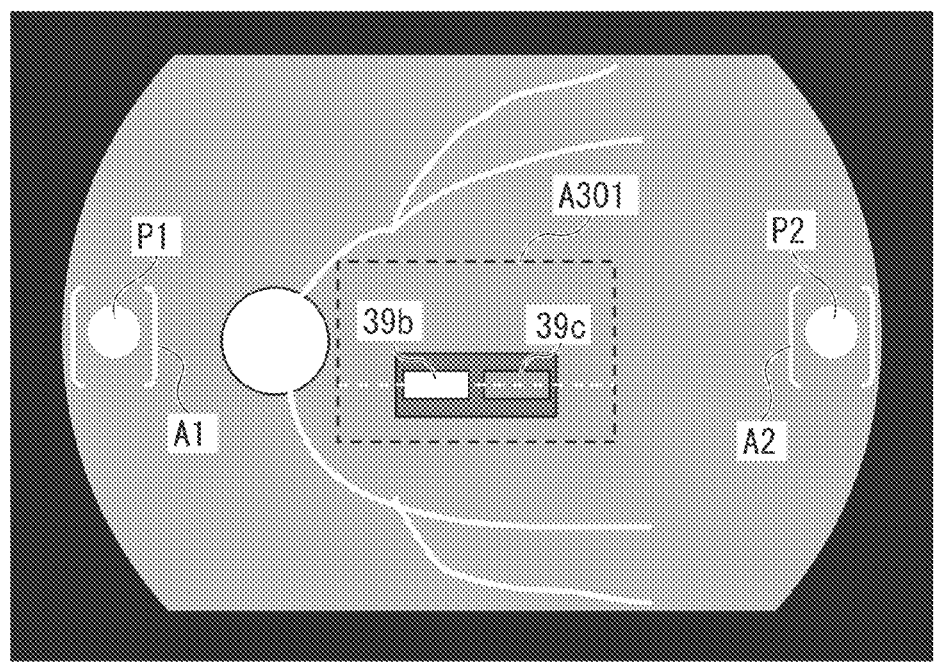
FIGS. 12A and 12B are diagrams each illustrating another example of a problem in the subject's eye, i.e., astigmatism, to be solved by the present exemplary embodiment.
Figure 12B:
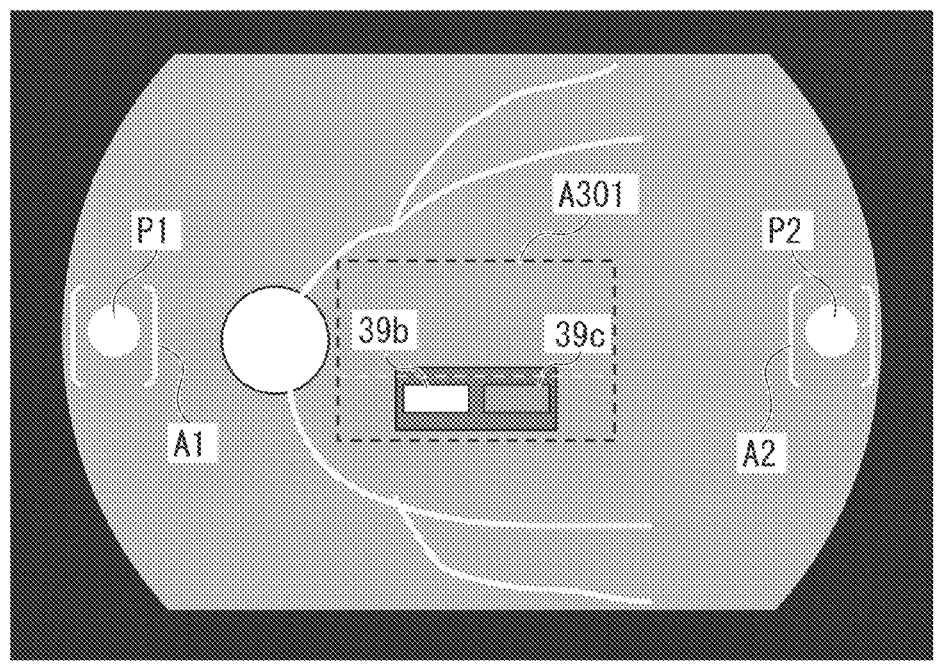

Problems to be solved by the present exemplary embodiment will be described referring to FIGS. 11A and 11B and FIGS. 12A and 12B. FIGS. 11A and 11B illustrate a case where a refractive error occurs in the subject's eye, and FIGS. 12A and 12B illustrate a case where the subject's eye suffers from astigmatism. FIG. 11A illustrates a case where the diopter of the subject's eye is 0, while FIG. 11B illustrates a case where the diopter of the subject's eye is −10. When the refractive power (diopter) of the subject's eye varies, a magnification produced by the apparatus changes. When this occurs, as long as a focusing index image is disposed at the center of an optical axis as in the case of the conventional technology, the influence of the magnification causes no positional shifting of a focusing index. Generally, in a fundus camera, the focusing index image is disposed at a position slightly shifted from the optical axis because of a white spot generated at an image center in many cases. Thus, as illustrated in FIG. 11B, when the diopter of the subject's eye varies, the change of the magnification causes a change in projection position of the focusing index. As a result, a focusing reference position of the focusing index image changes depending on the diopter of the subject's eye. FIG. 12A illustrates a case where the diopter of the subject's eye is −10, while FIG. 12B illustrates a case where the subject' eye has a diopter of −10 and suffers from astigmatism. When the subject' eye suffers from astigmatism, as long as the focusing index image is disposed at the center of an optical axis, the influence of the magnification causes no positional shifting of the focusing index while an aspect ratio of the focusing index image changes. However, for the aforementioned reason, since the focusing index image is disposed at the position slightly shifted from the optical axis, as illustrated in FIG. 12B, the projection position of the focusing index is changed because of the change of the horizontal and vertical magnification when the subject' eye suffers from astigmatism. The present exemplary embodiment is designed to solve this problem.

Figure 1:
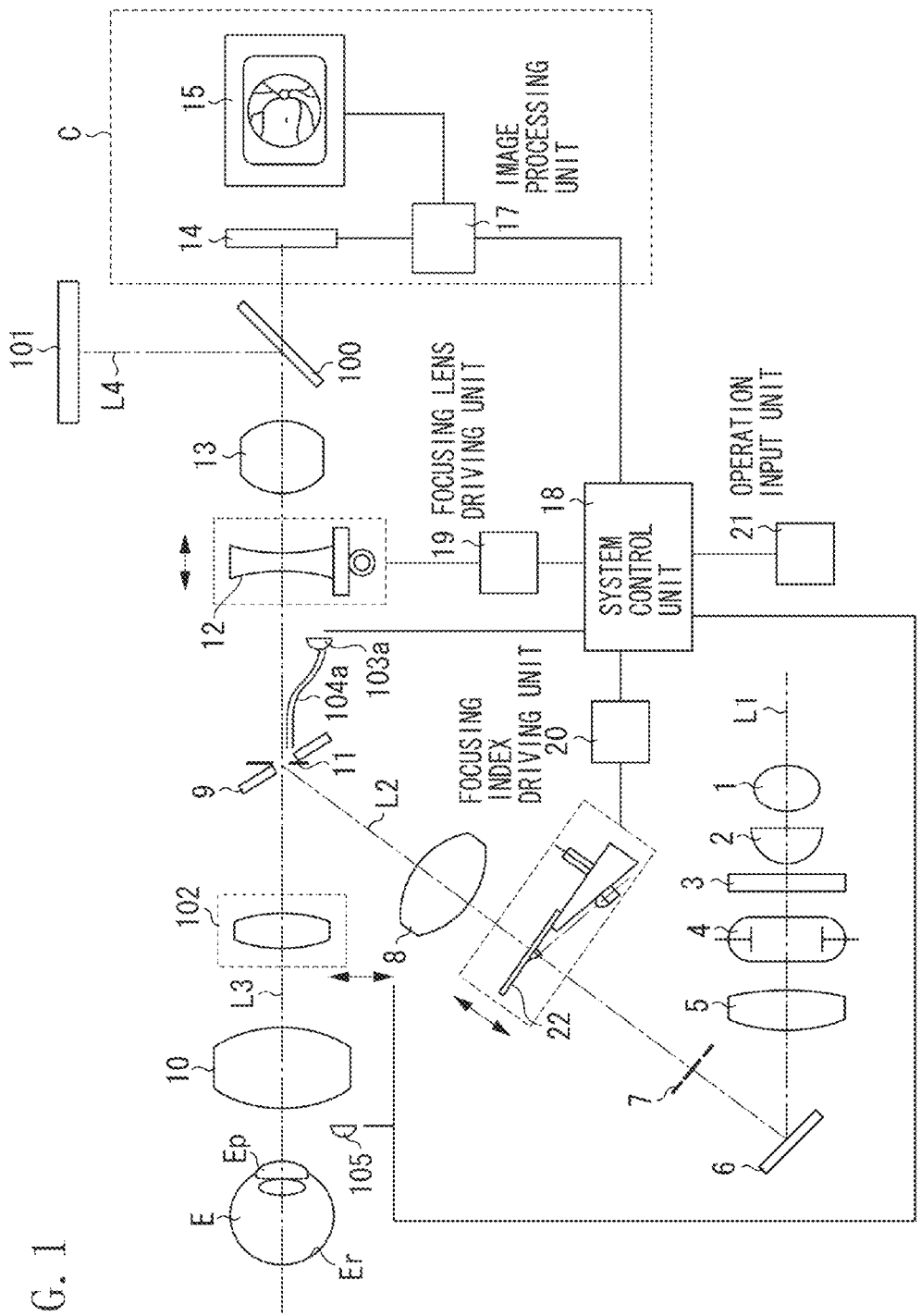
FIG. 1 is a diagram illustrating a configuration of an ophthalmologic apparatus according to a first exemplary embodiment.

FIG. 1 is a diagram illustrating a first configuration example of fundus camera that is an example of the ophthalmologic apparatus according to the present exemplary embodiment. An observation light source 1 such as a halogen lamp for emitting stationary light, a condenser lens 2, a filter 3 for transmitting infrared light while blocking visible light, a photographing light source 4 such as a flash unit, a lens 5, and a mirror 6 are arranged on an optical axis L1. A ring diaphragm 7 having a ring-shaped opening, a relay lens 8, and a perforated mirror 9 having a center opening are sequentially arranged on an optical axis L2 in a reflection direction of the mirror 6.

On an optical axis L3 in a reflection direction of the perforated mirror 9, an auxiliary lens 102 for observing an anterior segment and an objective lens 10 facing a subject's eye E are arranged. The auxiliary lens 102 can be inserted into or detached from the optical axis L3. A photographing diaphragm 11 arranged in a hole portion of the perforated mirror 9, a focusing lens 12 movable on the optical axis L3 to adjust focus, a photographing lens 13, and a half mirror 100 are also sequentially arranged on the optical axis L3. An image sensor 14 serving as an imaging unit for observing a moving image and capturing a still image in a photographing camera C is disposed ahead of the half mirror 100. An internal fixation lamp 101 is disposed ahead of an optical axis L4 in a reflection direction of the half mirror 100.

An exit end of a light guide 104a for guiding a light flux from a light emitting diode (LED) light source 103a is disposed in front of the perforated mirror 9. The exit end is set as an alignment index P1. The alignment index P1 is shifted from the optical axis L3, and an exit end of a light guide 104b (not illustrated) for guiding a light flux from an LED light source 103b (not illustrated) having a wavelength equal to that of the LED light source 103a is disposed at a position symmetrical to the alignment index P1 around the optical axis L3. This exit end is set as an alignment index P2. Accordingly, an alignment index projection optical system is configured.

A system control unit 18, which can be realized by, for example, a personal computer (PC), includes a central processing unit (CPU) 190 (not illustrated). The system control unit 18 mainly controls an operation of each component of the ophthalmologic apparatus. A main memory 110 (not illustrated) stores a control program executed by the system control unit 18, or provides a work region during program execution of the CPU 190. The system control unit 18 controls an image processing unit 17 and a focusing control unit 30. The system control unit 18 controls a focusing lens driving unit 19 serving as a driving unit, and a focusing index driving unit 20. The focusing lens driving unit 19 and the focusing index driving unit 20 are controlled based on an output signal of the focusing control unit 30, which has processed an image obtained by the image processing unit 17. The driving unit includes at least one of the focusing lens driving unit 19, the focusing index driving unit 20, and the focusing control unit 30.

An output of the image sensor 14 serving as an imaging unit is connected to the image processing unit 17, and the image processing unit 17 displays an observation image on a monitor 15 under control of the system control unit 18. The optical axis L3 indicates an optical axis of the photographing optical system, and the image sensor 14 serving as an imaging unit captures a fundus image of the subject's eye via the photographing optical system.

A focusing index projection unit 22 is disposed between the ring diaphragm 7 and the relay lens 8 on the optical axis L2. The focusing index projection unit 22 will be described in detail below.

The optical axes L1 and L2 are optical axes of an illumination optical system, and the projection unit 22 is disposed to be inserted into or detached from an optical path of the illumination system.

Under control of the system control unit 18, the focusing index projection unit 22 and the focusing lens 12 are interlockingly moved in the directions of the optical axis L2 and the optical axis L3, respectively, by the focusing lens driving unit 19 and the focusing index driving unit 20. Thus, at least one of the focusing lens driving unit 19 and the focusing index driving unit 20 serving as driving units is driven to change a position of at least one of the projection unit 22 and the focusing lens 12.

In a manual focusing mode, the system control unit 18 controls the focusing lens driving unit 19 and the focusing index driving unit 20 according to an operation input of an operation input unit 21. At this time, the focusing index projection unit 22 and the image sensor 14 serving as an imaging unit are in an optically conjugate relationship. In an automatic focusing mode, the system control unit 18 controls the focusing lens driving unit 19 and the focusing index driving unit 20 based on an output result of the focusing control unit 30.

Further, the system control unit 18 controls light amount adjustment and light turning ON/OFF of the observation light source 1 and light amount adjustment and light turning ON/OFF of the photographing light source 4.

Next, an operation according to the present exemplary embodiment will be described.

First, the system control unit 18 lights an anterior segment observation light source 105 in a light turned-OFF state of the observation light source 1. A light flux output from the anterior segment observation light source 105 is reflected and scattered in the anterior segment of the subject's eye E, and passes through the objective lens 10, the auxiliary lens 102, the photographing diaphragm 11, the focusing lens 12, the photographing lens 13, and the half mirror 100 to form an image on the image sensor 14. The image processing unit 17 displays the anterior segment image captured by the image sensor 14 on the monitor 15.

An operator performs rough adjustment of alignment between the subject's eye E and the optical unit while observing the anterior segment image displayed on the monitor 15, and then presses an alignment changing switch (not illustrated) in the operation input unit 21 to observe the fundus.

Then, the system control unit 18 separates the auxiliary lens 102 from the optical axis L3, and lights the observation light source 1 while turning a light OFF for the anterior segment observation light source 105. A light flux emitted from the observation light source 1 is condensed on the condenser lens 2, visible light is cut off by the filter 3, and only infrared light is transmitted. The light flux is transmitted through the photographing light source 4 such as a flash unit, converted into a ring light flux through the lens 5, the mirror 6, and the ring diaphragm 7, and then deflected in the direction of the optical axis L3 by the relay lens 8 and the perforated mirror 9 to illuminate the fundus Er of the subject's eye E. The light flux that has reached the fundus Er is reflected and scattered, exits from the subject's eye E, and then passes through the objective lens 10, the photographing diaphragm 11, the focusing lens 12, the photographing lens 13, and the half mirror 100 to form an image on the image sensor 14. The image processing unit 17 displays the fundus image captured by the image sensor 14 on the monitor 15.

The operator performs rough adjustment of alignment between the subject's eye E and the optical unit while observing the fundus image displayed on the monitor 15, performs focus adjustment, and then presses a photographing switch (not illustrated) in the operation input unit 21 to perform photographing. In the present exemplary embodiment, the apparatus will be described as an apparatus having an autofocus function for automatically executing focus adjustment.

To execute the automatic focusing function, the output of the image processing unit is connected to the system control unit 18, and to the focusing control unit 30. Further, an automatic focusing operation is performed by connecting the focusing control unit 30 to the focusing lens driving unit 19 and the focusing index driving unit 20.

A function of the focusing index projection unit 22 will be described.

Figure 7:
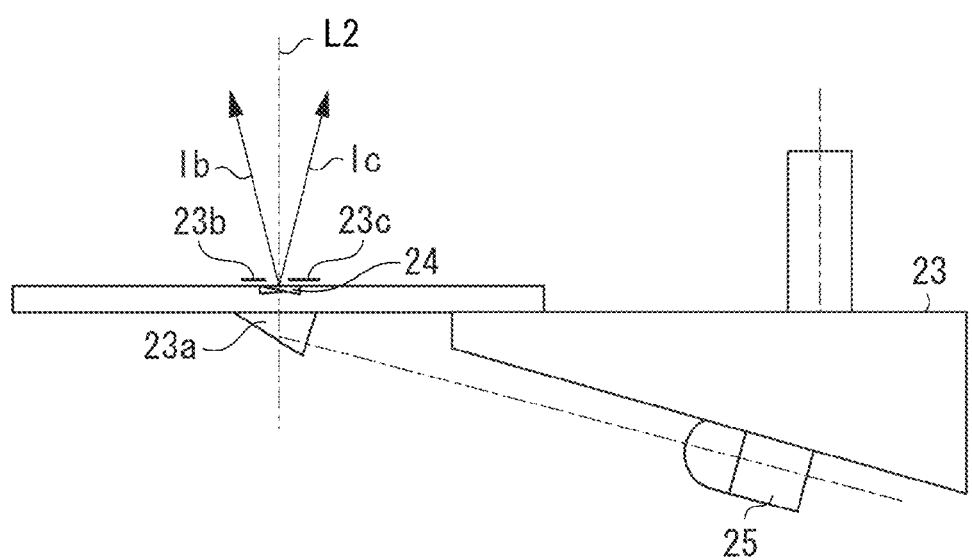
FIG. 7 is a diagram illustrating a focusing index image projection unit.
Figure 8:
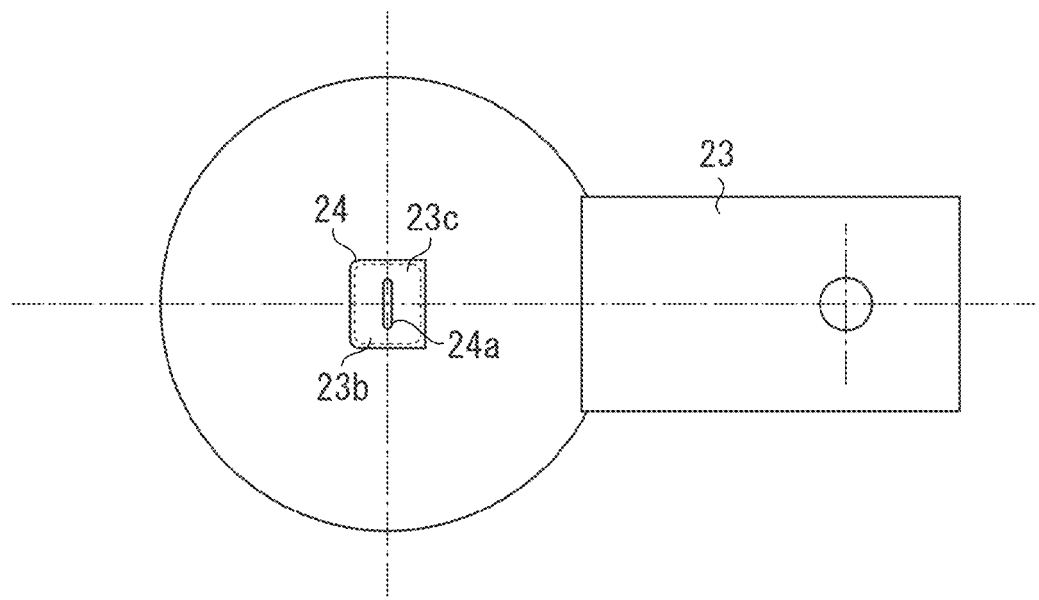
FIG. 8 is a diagram illustrating the focusing index image projection unit as viewed from an optical axis direction.

In FIG. 7, light fluxes from a focusing index illumination LED 25 are deflected in the direction of the optical axis L2 by a prism unit 23a of a focus split prism 23 to reach prism units 23b and 23c. The prism units 23b and 23c have prism planes of angles symmetrical to each other. The light fluxes that have reached the prism units 23b and 23c pass through a rectangular opening 24a of a focusing index mask portion 24 illustrated in FIG. 8 to be converted into two focusing index light fluxes Ib and Ic symmetrical with respect to the optical axis L2, and reach the subject's eye E as a plurality of focusing indices via the relay lens 8, the perforated mirror 9, and the objective lens 10.

Figure 9:
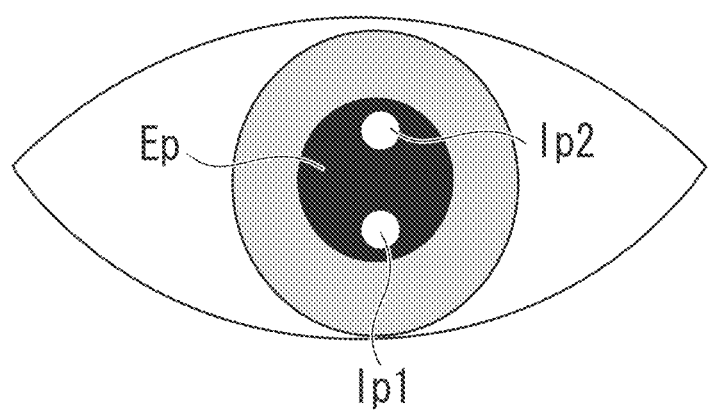
FIG. 9 is a diagram illustrating the position of a focusing index light flux on a subject's eye pupil.

FIG. 9 illustrates a position Ip1 of the focusing index light flux Ib on a pupil Ep of the subject's eye E and a position Ip2 of the focusing index light flux Ic on the pupil Ep of the subject's eye E.

Figure 10A:
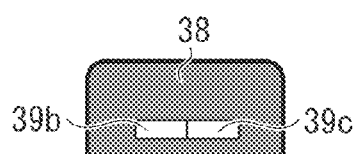
FIGS. 10A, 10B, and 10C are diagrams each illustrating the function of focusing indices.
Figure 10A:
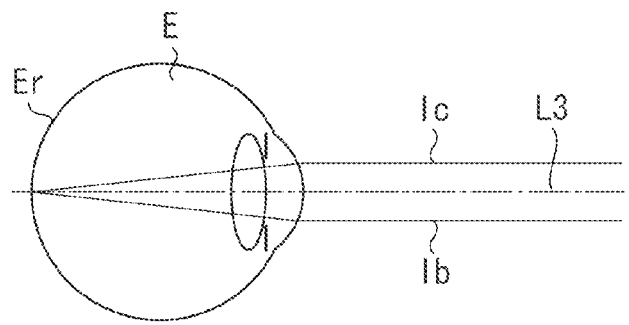
Figure 10B:
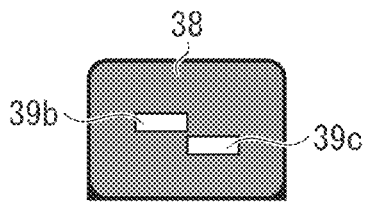
Figure 10B:
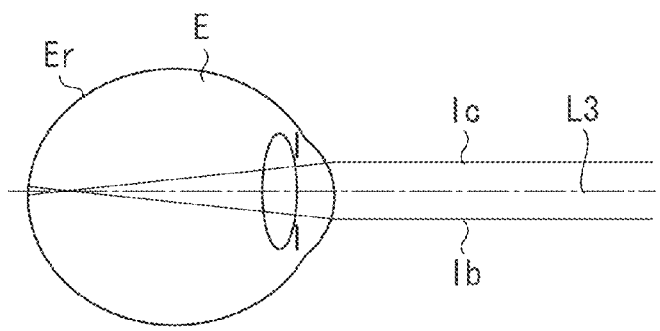
Figure 10C:
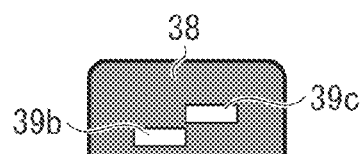
Figure 10C:
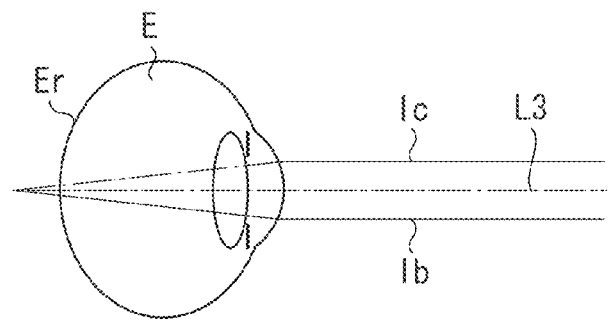

FIGS. 10A, 10B, and 10C illustrate reaching of the focusing index light fluxes Ib and Ic to the fundus Er of the subject's eye E and focusing index images 39b and 39c formed on the fundus Er by the focusing index light fluxes Ib and Ic. Each figure illustrates an image 38, formed on the fundus Er, of the focusing index mask portion 24.

FIG. 10A illustrates a case where the fundus Er of the subject's eye E and the focusing index mask portion 24 are in an optically conjugate relationship. Since the fundus Er and the focusing index mask portion 24 are in the optically conjugate relationship, the two separated focusing index light fluxes Ib and Ic fall on the fundus Er, and the images of the rectangular opening 24a of the focusing index mask portion 24 are projected onto the fundus to become focusing index images 39b and 39c, and arranged in a row based on a predetermined positional relationship. In this case, the projection unit 22 and fundus Er are also set in an optically conjugate relationship.

FIG. 10B illustrates a case where the subject's eye E is more myopic than that illustrated in FIG. 10A. In this case, since the fundus Er and the focusing index mask portion 24 are not in an optically conjugate relationship, the two separated focusing index light fluxes Ib and Ic become focusing index images 39b and 39c on the fundus Er, which are vertically shifted from each other. The focusing index image 39b is shifted upward, while the focusing index images 39c is shifted downward. FIG. 10C illustrates a case where the subject's eye E is more hyperopic than that illustrated in FIG. 10A.

In this case, since the fundus Er and the focusing index mask portion 24 are not in an optically conjugate relationship, the two separated focusing index light fluxes Ib and Ic become focusing index images 39b and 39c on the fundus Er, which are vertically shifted from each other. The focusing index image 39b is shifted downward, while the focusing index images 39c is shifted upward.

The focusing lens driving unit 19, which detects the focusing index images 39b and 39c and performs driving to change a position of the focusing lens 12, and the focusing index driving unit 20, which performs driving to change a position of the projection unit 22 having the focusing index mask portion 24, are linked with each other in focus to be operated.

Accordingly, the focusing index images 39b and 39c are arranged in a row, thereby setting the fundus Er and the focusing index mask portion 24 in an optically conjugate relationship. Since the focusing index mask portion 24 and the image sensor 14 are in the optically conjugate relationship, the fundus Er and the image sensor 14 are set in an optically conjugate relationship, thereby enabling focusing on the fundus Er.

Figure 2:
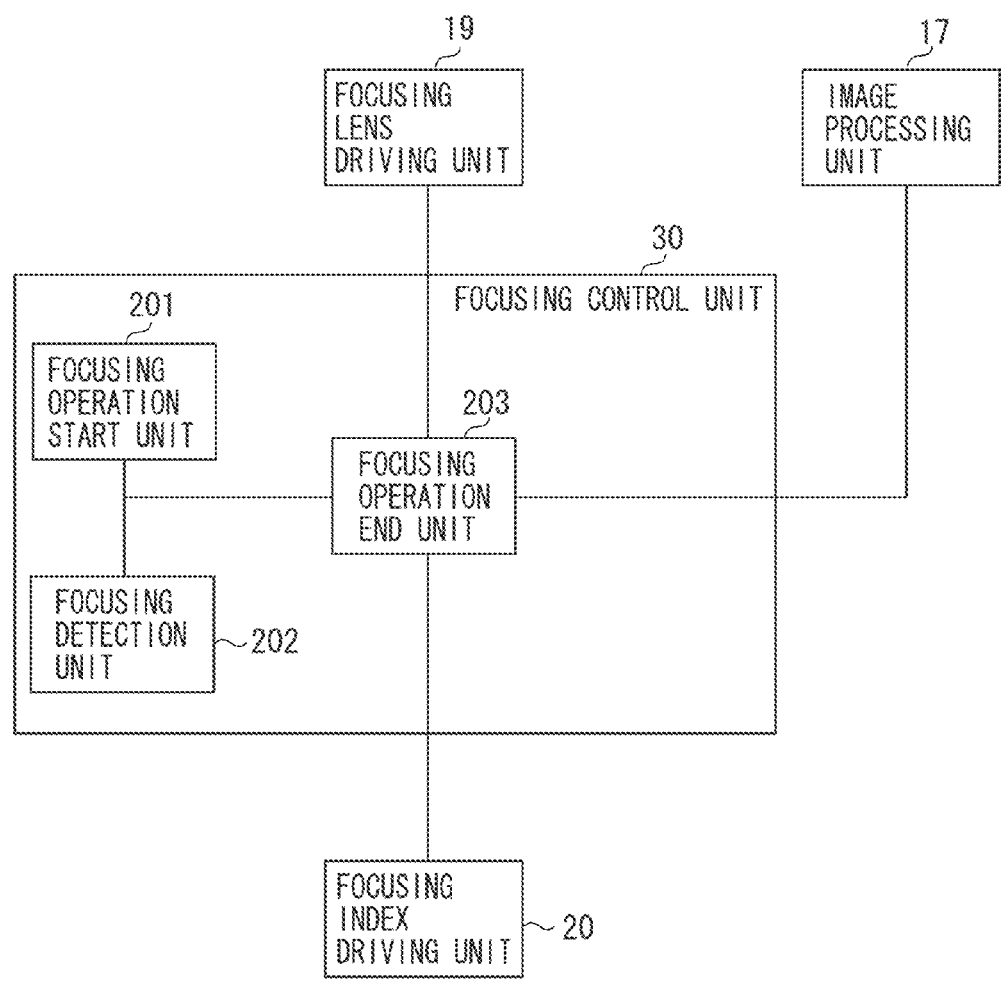
FIG. 2 is a diagram illustrating a characteristic configuration according to the first exemplary embodiment.

Next, referring to FIG. 2, the focusing control unit 30 for obtaining information necessary for focusing control to output a driving signal to the driving unit will be described.

The focusing control unit 30 includes a focusing operation start unit 201 used for focusing, a focusing detection unit 202, and a focusing operation end unit 203. The focusing operation start unit 201 and the focusing operation end unit 203 are connected to the focusing detection unit 202 to manage execution of a focusing operation.

The focusing detection unit 202, to which an image from the image processing unit 17 is input, can output signals to the focusing lens driving unit 19 and the focusing index driving unit 20 serving as the driving units. Accordingly, the configuration of the focusing control unit 30 enables management of the execution of the focusing operation by the focusing detection unit 202, which detects an in-focus state to output data for a focusing operation, the focusing operation start unit 201, and the focusing operation end unit 203.

Figure 3:
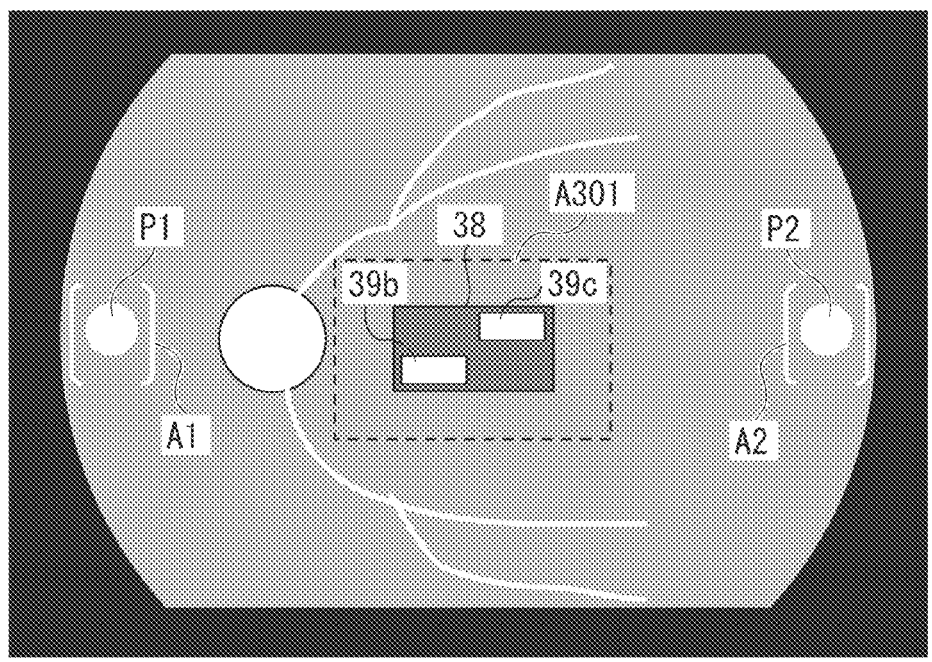
FIG. 3 is a diagram illustrating a fundus image displayed on a monitor.

First, to describe the autofocusing operation, a focusing detection position detected by the focusing detection unit 202 will be described referring to FIG. 3. FIG. 3 illustrates the fundus image displayed on the monitor 15, where a region A301 is a focusing detection position of the focusing detection unit 202. Thus, the region A301 includes an image 38 of the mask portion 24 including the focusing index images 39b and 39c.

The position of the region A301 is determined by a position onto which the focusing index mask portion 24 is projected on the fundus Er by the illumination optical system, and the size of the region A301 is determined by the prism plane angles of the prism units 23b and 23c and the magnification of the illumination optical system. Specifically, the size corresponds to a distance between the focusing index images 39b and 39c on the fundus Er when optical separation is largest within an assumed diopter range of the fundus Er or within a movable range of the focusing index projection unit 22. For example, when the diopter of the subject's eye is −10, the size of one prism unit is 0.4 mm (lengthwise direction)×0.05 mm (widthwise direction), a plane angle is 12°, an end of the diopter range is +15, and the magnification of the illumination optical system is 1, the size of the region A301 is approximately 0.8 mm (lengthwise direction)×1.25 mm (widthwise direction). The size of the focusing index mask portion 24 can be arbitrarily set. However, since the mask portion 24 is a light-blocking member in many cases, an image 38 of the mask portion 24 is generally smaller than the region A301.

FIG. 3 further illustrates alignment indices P1 and P2 used for performing alignment between the fundus camera and the subject's eye described above referring to FIG. 1, and guide frames A1 and A2 for the alignment indices P1 and P2.

Next, an operation of the focusing control unit 30 will be described referring to FIGS. 4A and 4B and FIG. 5.

Figure 4A:
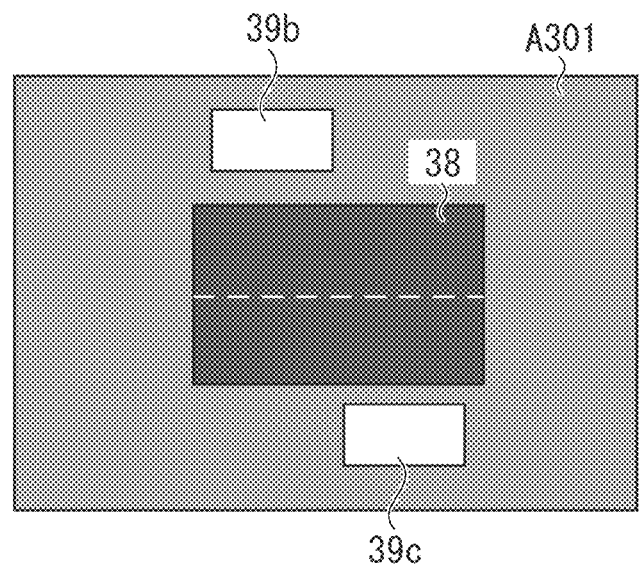
FIGS. 4A and 4B are diagrams each illustrating focusing position detection performed by a focusing operation unit.
Figure 5:
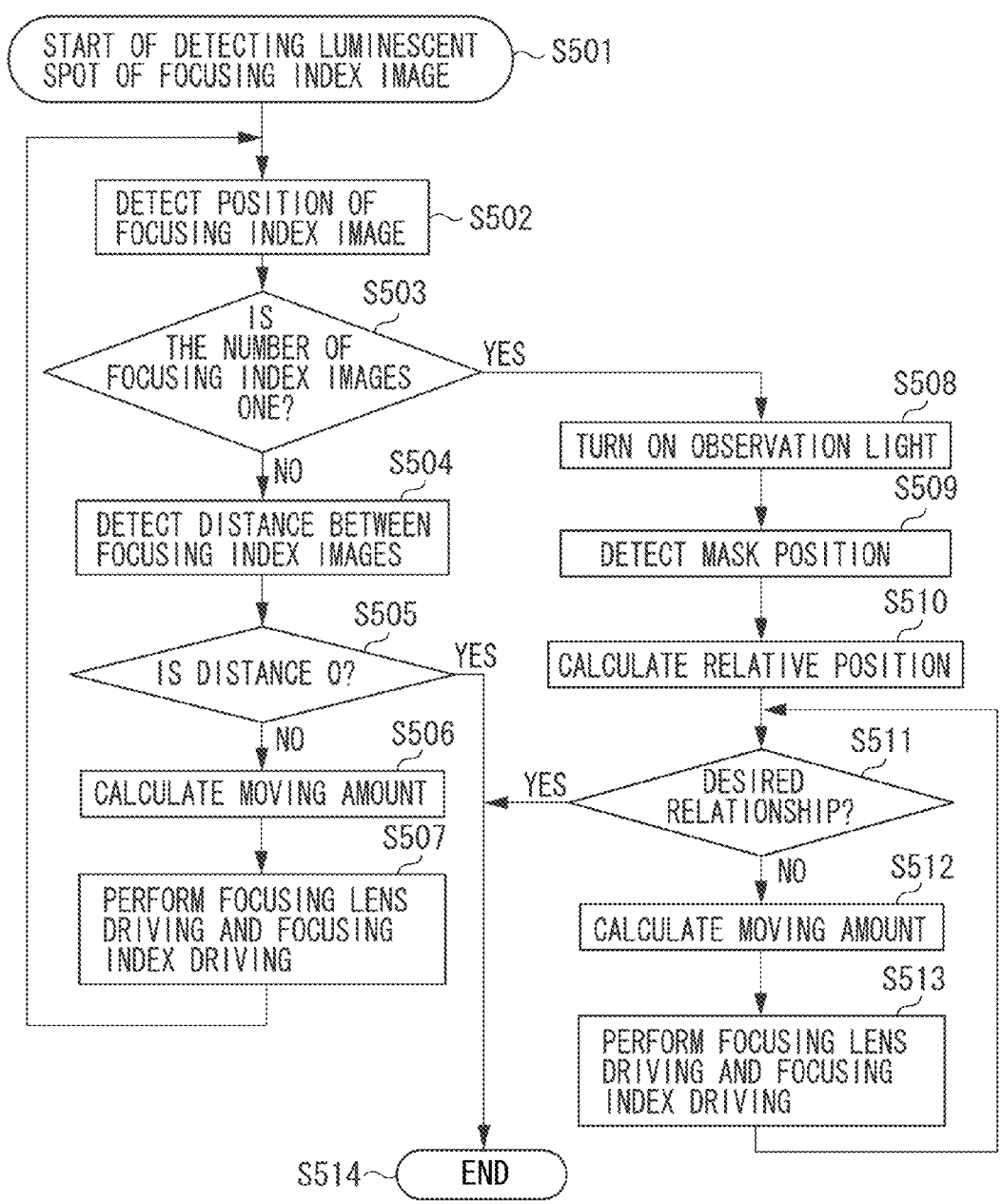
FIG. 5 is a flowchart illustrating processing performed by the focusing operation unit.

FIG. 4A illustrates a normal fundus photographing state.

Figure 4B:
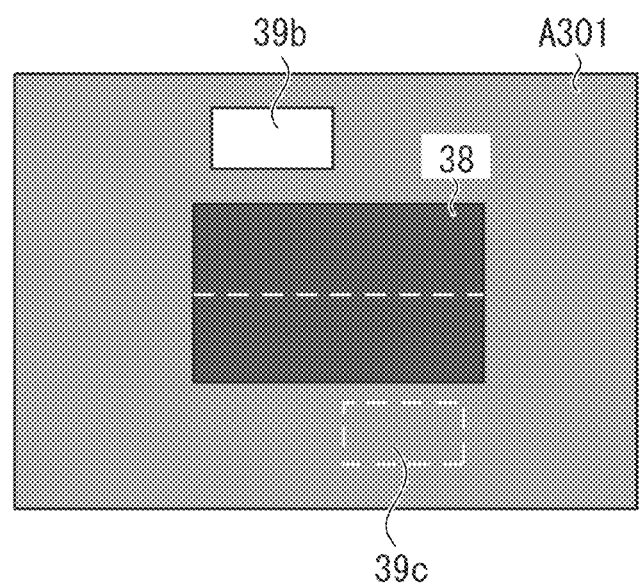

FIG. 4B illustrates a photographing state on the condition that a state of the subject's eye is bad, for example, the subject's eye has a small pupil, the focusing index light flux of one of the positions Ip1 and IP2 illustrated in FIG. 9 is vignetted at the pupil, or the focusing index light flux does not reach the fundus due to the opacity of optic media, such as cataract. Center dotted lines illustrated in FIGS. 4A and 4B indicate positions where the focusing index images 39b and 39c are arranged in a row when the camera is focused.

A focusing operation will be described referring to a flowchart illustrated in FIG. 5.

An operation when determination is made as to whether there is a plurality of focusing indices will be described below.

In step S501, the focusing operation start unit 201 starts position detection of luminescent spots of focusing index images projected on the fundus within the region A301. The focusing index images in this case are as illustrated in FIGS. 4A and 4B. In step S502, the focusing detection unit 202 detects a gray region from the left end of the focusing index image 39b to the right end of the focusing index image 39c illustrated in FIG. 4A or 4B. Then, in step S503, the focusing detection unit 202 performs vertical scanning in FIG. 4A or 4B to detect respective peak positions of the focusing index image 39b and the focusing index image 39c detected in step S502, and detects whether the number of recognizable focusing indices is one.

As described above, through the processing from step S501 to step S503, the focusing control unit 30 can calculate and detect the number of focusing indices based on the positional relationship between the focusing index image 39b and the focusing index image 39c.

An operation when the number of focusing indices is two or more will be described below.

In step S504, the focusing control unit 30 can calculate a distance based on the positional relationship between the focusing index image 39b and the focusing index image 39c, and detect a focusing position.

Then, in step S514, the focusing operation end unit 203 determines whether the distance calculated is zero in step S505. When zero (YES in step S505), the focusing operation of the focusing control unit 30 is ended. When not zero (NO in step S505), the focusing operation of the focusing control unit 30 is continued.

Then, in step S506, the focusing detection unit 202 calculates a moving amount corresponding to the distance calculated in step S504. In step S507, the focusing detection unit 202 outputs a driving signal indicating the moving amount calculated in step S506 to the focusing lens driving unit 19 and the focusing index driving unit 20 according to the system control unit 18, and changes the positions of the focusing lens and the projection unit 22.

As described above, the focusing operation executed in steps S503, S504, S506, and S507 by the focusing detection unit 202 is started in step S501 by the focusing operation start unit 201, and ended in step S514 by the focusing operation end unit 203.

An operation when the number of focusing indices is one will be described below.

In step S508, observation light of the illumination optical system is lit. Accordingly, when there is only one focusing index in the captured fundus image, illuminance to illuminate the projection unit 22 is increased as compared with a case where there is a plurality of focusing indices in the fundus image. Thus, the focusing index mask portion 24 is projected onto the fundus of the subject's eye with higher contrast, thereby facilitating detection of an outer shape of the mask portion 24. The mask portion 24 is made of a material, such as metal, not transmitting light. Then, in step S509, a projection region of the mask portion 24 on the fundus is detected. The mask portion has a linear outer shape and characteristics of lower luminance than other regions, because the amount of light transmitted through the mask portion is decreased. The region of the mask portion 24 can be detected by performing edge detection processing such as differential processing using the characteristics. When the fundus and the mask portion 24 are optically conjugate with each other, the focusing index image is positioned at the center position (indicated by white dotted lines in FIGS. 4A and 4B) of an image 38 of the focusing index mask portion 24.

In step S510, a relative positional relationship (distance) between the focusing index image 29b and the focusing index mask portion 24 is calculated. By detecting a focusing position, information about a positional relationship between the center position of the mask portion 24 and the focusing index image can be obtained. In place of the focusing index image 39b, the focusing index image 39c can be used. If a shadow of the mask portion 24 can be detected without lighting the observation light of the illumination optical system in step S508, focusing processing can be performed.

Then, in step S511, the focusing operation end unit 203 determines whether the distance calculated in step S510 is a desired value. When the distance is the desired value (YES in step S511), the focusing operation of the focusing control unit 30 is ended. When not the desired value (NO in step S511), the focusing operation of the focusing control unit 30 is continued. The desired value is a value determined by a position relative to the projection unit 22, and is equal to a relative positional relationship between members when an image is formed at the fundus position of the subject's eye. For example, the desired value is equal to a relative positional relationship between the mask portion 24 and the opening 24a illustrated in FIG. 8. In other words, for the image on the fundus, the focusing operation is performed so that the center position of the mask portion 24 and the position of the focusing index can be equal.

Then, in step S512, the focusing detection unit 202 calculates a moving amount corresponding to the distance calculated in step S510. In step S513, the focusing detection unit 202 outputs a driving signal indicating the moving amount calculated in step S512 to the focusing lens driving unit 19 and the focusing index driving unit 20 according to the system control unit 18, and changes the positions of the focusing lens and the projection unit 22.

As described above, the focusing operation executed in steps S510, S511, S512, and S513 by the focusing detection unit 202 is started in step S501 by the focusing operation start unit 201, and ended in step S514 by the focusing operation end unit 203.

Figure 6:
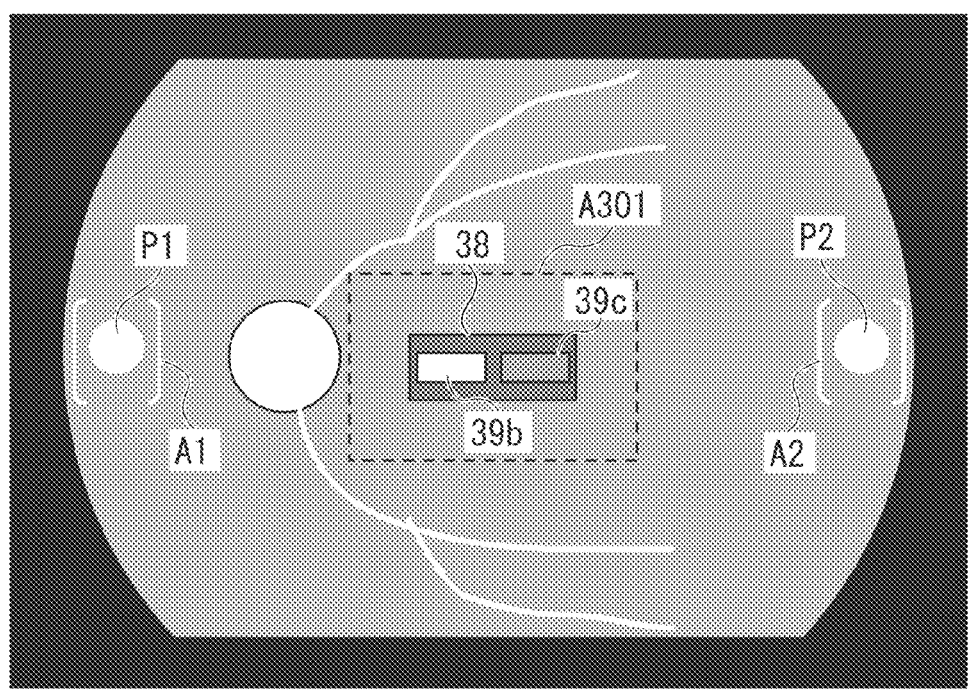
FIG. 6 is a diagram illustrating a fundus image displayed on the monitor at the time of completion of focusing and alignment.

After the end of the focusing operation, an observation image illustrated in FIG. 6 is displayed on the monitor 15. For simpler description, it is assumed that the focusing index 39c is vignetted because of the state of the subject's eye, the alignment indices P1 and P2 are within the guide frames A1 and A2, and fine adjustment of alignment between the subject's eye E and the optical unit has been completed. An in-focus image suited to radiographic image interpretation can be obtained by performing photographing in this state. Thus, autofocusing can be performed even when there is only one focusing index on the fundus image. As a result, autofocusing can be performed even when a state of the subject's eye is not good, such as a small pupil or cataract. Since focusing is carried out based on information about the positional relationship between the projection unit 22 and the projection position of the focusing index on the fundus, focusing can be performed with stable accuracy even when the position of the projection unit 22 changes from one individual difference to another due to an individual difference of refractive power of the eye.

When there is a plurality of focusing indices on the fundus, more stable autofocusing can be carried out by using a positional relationship among the plurality of indices. Thus, stable focusing can be performed by changing a focusing method between when there is only one focusing index on the fundus and when there is a plurality of focusing indices on the fundus.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-257553 filed Nov. 26, 2012, which is hereby incorporated by reference herein in its entirety.

What is claimed is:

1. An ophthalmologic apparatus comprising:
a photographing optical system configured to photograph a fundus of a subject's eye via a focusing lens;
a projection unit configured to project a plurality of focusing indices corresponding to an opening of a mask portion;
a detecting unit configured to detect if there is one or a plurality of focusing index images in a fundus image of the subject's eye; and
a driving unit configured to drive the focusing lens along an optical path
using information about positions of the plurality of focusing index images corresponding to the opening of the mask portion when the plurality of focusing index images is detected in the fundus image; and
to drive the focusing lens along the optical path using information about both a position of an image corresponding to the mask portion different from the opening of the mask portion and a position of a focusing index image corresponding to the opening of the mask portion when one focusing index image of the plurality of focusing index images is detected in the fundus image.

2. The ophthalmologic apparatus according to claim 1, wherein the driving unit is configured to drive, when the plurality of focusing index images is detected in the fundus image, the focusing lens along the optical path so that a predetermined positional relationship is set among the plurality of focusing indices in the fundus image.

3. The ophthalmologic apparatus according to claim 2, wherein when the fundus of the subject's eye and the projection unit are optically conjugate with each other, the predetermined positional relationship is set among the plurality of focusing indices in the fundus image of the subject's eye.

4. The ophthalmologic apparatus according to claim 1, wherein the driving unit is configured to change a position of the projection unit in conjunction with a position of the focusing lens.

5. The ophthalmologic apparatus according to claim 1, further comprising an illumination optical system configured to illuminate the fundus of the subject's eye, wherein the projection unit is disposed to be insertable into and detachable from an optical path of the illumination optical system.

6. The ophthalmologic apparatus according to claim 1, wherein when one focusing index image of the plurality of focusing index image is detected in the fundus image, illuminance of illuminating the projection unit is higher than that when the plurality of focusing index images is detected in the fundus image.

7. The ophthalmologic apparatus according to claim 1, wherein, when one focusing index image of the plurality of focusing index images is detected in the fundus image, the driving unit is configured to drive the focusing lens along the optical path using information about both the position of the image corresponding to the mask portion and the position of the focusing index image so that the projection unit and an imaging unit in the photographing optical system become approximately conjugate with each other.

8. The ophthalmologic apparatus according to claim 1,
wherein the opening of the mask portion is rectangular, and
wherein the projection unit includes a prism having prism planes of angles symmetrical to each other arranged at the opening of the mask portion, and wherein light fluxes transmitted through the prism planes pass through the rectangular opening of the mask portion and are projected as a plurality of focusing indices onto the fundus.

9. The ophthalmologic apparatus according to claim 1, further comprising a focusing control unit configured to extract a region of the mask portion and a position of the focusing index from the fundus image, and to output a driving signal to the driving unit using information about a positional relationship between the extracted region and position.

10. The ophthalmologic apparatus according to claim 9, wherein the focusing control unit is configured to extract the region of the mask portion and the position of the focusing index from the fundus image of the subject's eye, and to output the driving signal to the driving unit so that a center of the opening for projecting the focusing index and the position of the focusing index substantially coincide with each other.

11. A method for controlling an ophthalmologic apparatus that includes a photographing optical system configured to photograph a fundus of a subject's eye via a focusing lens and a projection unit configured to project a plurality of focusing indices corresponding to an opening of a mask portion, the method comprising:
  detecting if there is one or a plurality of focusing index images in a fundus image of the subject's eye;
  driving the focusing lens along an optical path using information about positions of the plurality of focusing index images corresponding to the opening of the mask portion when the plurality of focusing index images is detected in the fundus image; and
  driving the focusing lens along an optical path using information about both a position of an image corresponding to the mask portion different from the opening of the mask portion and a position of a focusing index image corresponding to the opening of the mask portion when one focusing index image of the plurality of focusing index images is detected in the fundus image.

12. A computer-readable storage medium storing a program that causes a computer to perform the method according to claim 11.

13. An ophthalmologic apparatus comprising:
  a photographing optical system configured to photograph a fundus of a subject eye via a focusing lens;
  a projection unit configured to project a plurality of focusing indices corresponding to an opening of a mask portion;
  a detecting unit configured to detect if there is one or a plurality of focusing index images in a fundus image of the subject's eye; and
  a driving unit configured to drive, when one focusing index image of the plurality of focusing index images is detected in the fundus image, the focusing lens along an optical path using information about both a position of an image corresponding to the mask portion different from the opening of the mask portion and a position of a focusing index image corresponding to the opening of the mask portion,
  wherein illuminance for illuminating the projection unit is higher when one focusing index image of the plurality of focusing index images is detected in the fundus image as compared to illuminance for illuminating the projection unit when the plurality of focusing index image is detected in the fundus image.

14. The ophthalmologic apparatus according to claim 13, wherein the driving unit is configured to drive the focusing lens along the optical path so that a center position of the image corresponding to the mask portion different from the opening of the mask portion and the position of the focusing index image substantially coincide with each other.

15. The ophthalmologic apparatus according to claim 13, wherein luminance of the image corresponding to the mask portion is lower than luminance of an image corresponding to a region outside the mask portion.

16. An ophthalmologic apparatus comprising:
  an illumination optical system configured to illuminate a fundus of a subject's eye;
  a photographing optical system configured to photograph the fundus via a focusing lens using return light from the fundus illuminated by the illumination optical system;
  a projection unit configured to project a focusing index corresponding to an opening of a mask portion; and
  a driving unit configured to drive, using information about a relative positional relationship between an image corresponding to the mask portion different from the opening of the mask portion and a focusing index image corresponding to the opening of the mask portion, the focusing lens along an optical path of the photographing optical system and the projection unit along an optical path of the illumination optical system.

17. The ophthalmologic apparatus according to claim 16, wherein the driving unit is configured to drive the focusing lens and the projecting unit so that a center position of the image corresponding to the mask portion and the position of the focusing index image substantially coincide with each other.

18. A method for controlling an ophthalmologic apparatus comprising an illumination optical system configured to illuminate a fundus of a subject's eye, a photographing optical system configured to photograph the fundus via a focusing lens using return light from the fundus illuminated by the illumination optical system, and a projection unit configured to project a focusing index corresponding to an opening of a mask portion; the method comprising
  driving, using information about a relative positional relationship between an image corresponding to the mask portion different from the opening of the mask portion and a focusing index image corresponding to the opening of the mask portion, the focusing lens along an optical path of the photographing optical system and the projection unit along an optical path of the illumination optical system.

19. The method according to claim 18, wherein the focusing lens and the projection unit are driven so that a center position of the image corresponding to the mask portion and a position of the focusing index image substantially coincide with each other.

20. A method for controlling an ophthalmologic apparatus that includes a photographing optical system configured to photograph a fundus of a subject's eye via a focusing lens and a projection unit configured to project a plurality of focusing indices corresponding to an opening of a mask portion, the method comprising:

detecting if there is one or a plurality of focusing index images in a fundus image of the subject's eye; and driving, when one focusing index image of the plurality of focusing index images is detected in the fundus image, the focusing lens along an optical path using information about both a position of an image corresponding to the mask portion different from the opening of the mask portion and a position of a focusing index image corresponding to the opening of the mask portion, wherein illuminance for illuminating the projection unit is higher when one focusing index image of the plurality of focusing index images is detected in the fundus image as compared to illuminance for illuminating the projection unit when the plurality of focusing index images is detected in the fundus image.

21. A computer-readable storage medium storing a program that causes a computer to perform the method according to claim 18.

22. A computer-readable storage medium storing a program that causes a computer to perform the method according to claim 20.

23. The ophthalmologic apparatus according to claim 16, further comprising a calculating unit configured to calculate a distance between a center position of the image corresponding to the mask portion and the focusing index image to obtain the relative positional relationship, wherein the driving unit is configured to drive the focusing lens and the projection unit using the obtained relative positional relationship.

24. The method according to claim 18, further comprising calculating a distance between a center position of the image corresponding to the mask portion and the focusing index image to obtain the relative positional relationship, wherein the focusing lens and the projection unit are using the obtained relative positional relationship.

25. The ophthalmologic apparatus according to claim 16, further comprising a calculating unit configured to calculate the relative positional relationship, wherein the driving unit is configured to drive the focusing lens and the projection unit using the calculated relative positional relationship.

26. The method according to claim 18, further comprising calculating the relative positional relationship, wherein the focusing lens and the projection unit are driven using the calculated relative positional relationship.

27. The ophthalmologic apparatus according to claim 16, wherein the driving unit is configured to drive the focusing lens and the projection unit simultaneously using the information.

28. The method according to claim 18, wherein the focusing lens and the projection unit are simultaneously driven using the information.

* * * * *